United States Patent [19]

Rodbard et al.

[11] Patent Number: 4,468,383
[45] Date of Patent: Aug. 28, 1984

[54] DIMERIC ENKEPHALINS

[75] Inventors: David Rodbard, Bethesda; Y. Shimohigashi, Rockville; Hao-Chia Chen, Gaithersburg, all of Md.; Tommaso Costa, Munich, Fed. Rep. of Germany

[73] Assignee: The United States of America as represented by the Secretary of the Department of Health and Human Service, Washington, D.C.

[21] Appl. No.: 427,857

[22] Filed: Sep. 29, 1982

[51] Int. Cl.$^3$ .................... A61K 37/00; C07C 103/52
[52] U.S. Cl. ............................ 424/177; 260/112.5 R
[58] Field of Search ................. 424/177; 260/112.5 R

[56] References Cited

U.S. PATENT DOCUMENTS 4,178,284 12/1979 Sarantakis .................... 260/112.5 R
4,198,398 4/1980 Hudson ............................... 424/177

OTHER PUBLICATIONS

Y. Shimohigashi, T. Costa, S. Matsuura, H. C. Chen, D. Rodbard "Dimeric enkephalins display enhanced affinity and selectivity for the *delta* opiate receptor", *Mol. Pharm.* 21: 558-563 (1982).
Y. Shimohigashi, T. Costa, S. Matsuura, H. C. Chen, D. Rodbard "Peptides-Synthesis-Structure-Function", *Proc. Seventh American Peptide Symposium;* published Nov. 1981 by the Pierce Chemical Co.

*Primary Examiner*—Delbert R. Phillips
*Attorney, Agent, or Firm*—Holman & Stern

[57] ABSTRACT

The compounds of the invention are symmetrical dimers of enkephalin polypeptides comprising enkephalin polypeptide monomers linked at the C-termini thereof with a difunctional amino bridging group. The compounds are useful as investigative tools for probing the opiate receptor membranes, particularly as radiolabelled ligands for exploring the delta opiate receptor, and also have particular use as narcotic and/or analgesic agents.

20 Claims, 2 Drawing Figures

DIMERIC ENKEPHALINS

BACKGROUND OF THE INVENTION

The enkephalin polypeptides, methionine-enkephalin and leucine-enkephalin are well-known analgesics endogenous to brain tissue, originally identified and isolated by Hughes (*Brian Research*, 88:295–308, 1975 and *Nature*, 258:577–579, 1975). Numerous analogues and derivatives of the enkephalins have since been developed which variously act as agonists or antagonists of endogenous opiate peptides by binding to opiate receptors of neural tissues. The prior art enkephalin modifications, however, have not exhibited marked specificity for binding sites. Further, prior art enkephalin analogues have frequently lacked sufficient affinity for the receptor molecules, and are susceptible to enzymatic degradation.

SUMMARY OF THE INVENTION

The compounds of the invention are symmetrical dimers of enkephalin polypeptides comprising enkephalin polypeptide monomers linked at the C-termini thereof with a difunctional amino bridging group. The dimerization permits the enkephalin peptides to bind two opiate receptors simultaneously, thus providing a more rapid rate of association, higher affinity, and higher specificity for binding sites than their monomeric analogues or known drugs, opiate alkaloids, or prior art enkephalin derivatives. Many of the dimeric enkephalins of the invention have a high selectivity for the delta enkephalin receptor of the brain, and a higher affinity for this receptor than prior art analogues. The compounds are also resistant to enzymatic degradation by enkephalinases and other proteases in brain tissues, cells, and membranes. Thus, the compounds are extremely useful as investigative tools for probing the opiate receptor membranes, particularly as radiolabelled ligands for exploring the delta opiate receptor, and also have particular use as narcotic and/or analgesic agents.

DETAILED DESCRIPTION OF THE INVENTION

Figure 1:
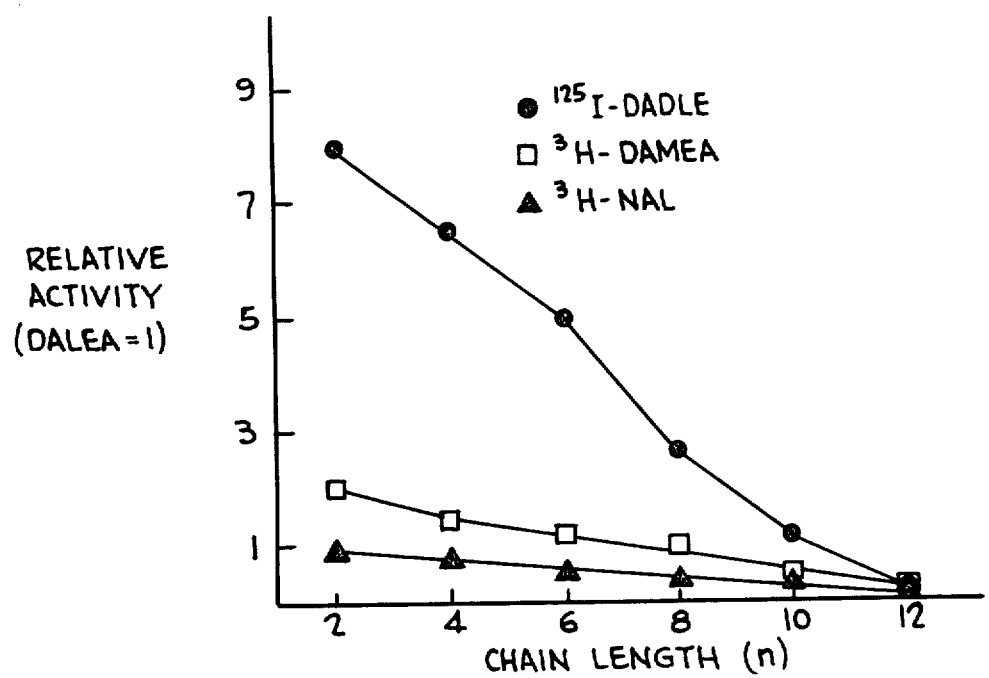
FIG. 1 is a graph of relative activity of $DPE_n$ in three radioligand assays as a function of chain length (n), expressed relative to DALEA.

The dimeric enkephalin analogues of the present invention comprise symmetrical dimers of precursor carboxyl-terminal enkephalin polypeptide monomers linked at the C-termini thereof with a diamino bridging group especially hydrazine, 2,7-diaminofluorene or diaminoalkane. The enkephalin polypeptide monomer precursors are leucine enkephalin (H-Tyr-D-Ala-Gly-Phe-Leu-OH), or di-, tri-, or tetrapeptide acid fragments thereof characterized by the following formula:

R—OH wherein R is selected from one of the following α-amino acid residue sequences: H-Tyr-D-Ala-Gly-Phe-Leu; H-Tyr-D-Ala-Gly-Phe; H-Tyr-D-Ala-Gly; and Phe-Leu; wherein Tyr is tyrosine, Ala is alanine, Gly is glycine, Phe is phenylanine, and Leu is leucine.

The monomeric precursors R-OH are dimerized or linked with a diamino bridging compound of the formula $H_2N-X-NH_2$, to form compounds of the formula:

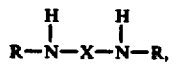

wherein the R groups are the same, and are as defined above.

The bridging moiety —X— is a direct bond,

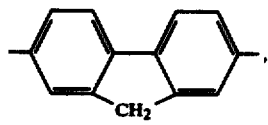

or alkylene having from 1 to 22 carbon atoms. The alkylene group may be branched or unbranched; substituted or unsubstituted; or uninterrupted or interrupted by heteroatoms, especially —O—, —S—, or —NH—, or groups such as carbonyl, carboxy, or carboxyamide, with the caveat that the dimers retain the capability of binding to neural opiate receptors. Particularly preferred groups are unbranched, unsubstituted, uninterrupted alkyl groups comprising polymethylene chains —$(CH_2)_n$—, wherein n is from 1 to 22.

Specific exemplary compounds within the scope of the invention comprise (a) Dimeric pentapeptide enkephalins (DPE) of the formula:

wherein R is H-Tyr-D-Ala-Gly-Phe-Leu and n is 1 to 22, preferably 1 to 12;

(b) Dimeric tetrapeptide enkepahlins (DTE) of the formula:

wherein R is H-Tyr-D-Ala-Gly-Phe and n is 1 to 22;

(c) Dimeric tripeptide enkephalins (DTrE) of the formula:

wherein R is H-Tyr-D-Ala-Gly and n is 1 to 22;

(d) Dimeric dipeptide enkephalins (DDE) of the formula:

wherein R is Phe-Leu and n is 1 to 22, preferably 1 to 12;

(e) Pentapeptide enkephalin dimers of the formula:

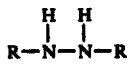

wherein R is H-Tyr-D-Ala-Gly-Phe-Leu; and (f) Pentapeptide enkephalin dimers of the formula:

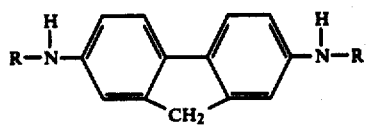

wherein R is H-Tyr-D-Ala-Gly-Phe-Leu.

Compounds exhibiting a particularly good affinity and selectivity for the delta opiate receptor are

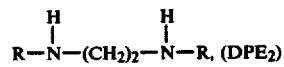

wherein R is the pentapeptide H-Tyr-D-Ala-Gly-Phe-Leu; and

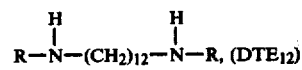

wherein R is the tetrapeptide H-Tyr-D-Ala-Gly-Phe. Owing to the selectivity and relative activities of these compounds they are especially useful as probes of the opiate receptor for membranes when radio-labelled by well known techniques such as tritium exchange or ($^{125}$I) iodination.

The compounds of the invention are broadly synthesized by linking two N-protected polypeptide acid precursors via the desired diamino bridging group to form the corresponding diamide. Preferably, the dimeric penta- and tetrapeptides are prepared in two stages: by condensing an appropriate N-protected dipeptide acid with the requisite bridging group, and then elongating the α-amino acid sequences of the resultant intermediate after deprotection. The α-amino acid sequences of the precursor polypeptides are obtained in a known fashion by conventional liquid phase techniques, as exemplified by Bodanszky, et al., in *Peptide Synthesis*, Wiley Interscience, N.Y. (1966). Various methods are known for protecting the terminal α-amino groups from undesired reaction during synthesis, most especially the use of blocking groups such as tert-butoxycarbonyl (Boc) or carbobenzoxy.

The enkephalin polypeptide acid precursors synthesized according to the prior art are condensed with the bridging groups according to the following scheme:

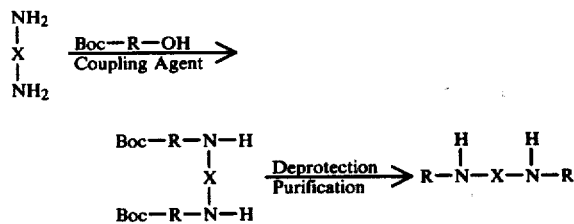

Preferably, at least when R is H-Tyr-D-Ala-Gly-Phe-Leu or H-Tyr-D-Ala-Gly-Phe, the dimers are prepared by two-step coupling. In this method of preparation, an N-protected dipeptide acid corresponding to the two (2) C-terminal amino acids of the α-amino acid sequence R is first reacted with the diamino bridging compounds to form an enkephalin amide intermediate. The α-amino acid sequences of the intermediate are then elongated to form the desired R group by deprotecting the α-amino groups of the intermediate followed by coupling with the appropriate N-protected di- or tripeptide acid. The following is an exemplary scheme for dimeric pentapeptide enkephalins according to the invention:

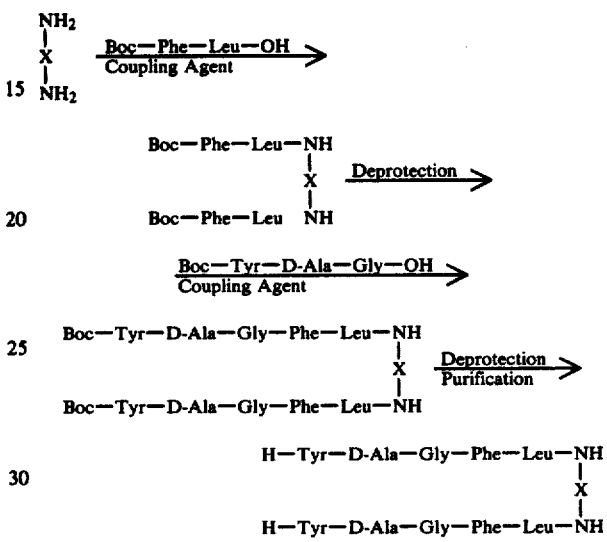

Suitable coupling agents are well known in the art and include, for example, water-soluble carbodiimides which activate the terminal carboxyl groups of the reactive peptide acids. The most widely used carbodiimides for this purpose are $EDC$ [1-ethyl-3-(3-dimethylaminopropyl) carbodiimide] and DCCI (dicyclohexylcarbodiimide). The coupling reaction is generally carried out in an organic solvent such as methylene chloride, dimethylformamide, or dioxane. A particularly useful system for the dimerization of the present invention is $EDC$ in dimethylformamide. To minimize racemization during coupling, additives such as 1-hydroxybenzotriazole (HOBt) are included in the reaction mixture. This is particularly important in the first step of the two-stage procedure when leucine is present.

The N-protecting groups are removed by any customary deprotecting agent such as trifluoroacetic acid or HBr in acetic acid. The product dimers are purified by conventional methods, usual gel filtration over SEPHADEX polydextran gels, suitably a SEPHADEX G-25 gel. The gels are prepared as usual and eluted with a suitable eluant such as 30% acetic acid.

The dimeric enkephalin analogues bridged by methylene chains are particularly useful in the elucidation of the physiological role of 'δ' (peptide) and 'μ' (alkaloid) opiate receptors of the brain and other neural tissues, owing to the extremely high δ selectivity of many of the compounds. These analogues also exhibit a strong affinity for the δ receptors, and a loss of binding activity for the μ receptors. Since the corresponding monomers generally exhibit a relatively low affinity and little or no selectivity for δ receptors over μ receptors, it is believed that the affinity and selectivity of these dimeric ligands is at least in part attributable to the property of selectively crosslinking δ but not μ receptor, sites. The result is particularly surprising owing to the known phenomenon that structural modifications or abolition of the C-terminal free carboxyl group in monomeric enkephalins invariably leads to loss of δ selectivity and gain of μ activity. While the diaminofluorene and hydrazine bridged compounds exhibit little or no delta selectivity they are useful as biochemical probes of the properties and structure-activity relationship of the enkaphalin receptors.

The enkephalin analogues are thus useful as radioligands in probes of the opiate receptor membranes. Further, the dimers function as high-potency endogenous opiate peptide agonists or antagonists, with pharmaceutical analgesic activity organtagonistic activity toward known opiate drugs.

The bioactivity of the present dimeric enkephalins was established using the classical bioassays for opiate activity, the guinea pig ileum (GPI) assay and the mouse vas deferens (MVD) assay. There was an excellent general correlation between activity in delta receptor assays (infra) and the MVD assay. Dimeric pentapeptide enkephalin $DPE_2$ [$X=-(CH_2)_2-$]was the most potent in the MVD assay, with activity surpassing that of the corresponding pentapeptide monomer. $DPE_2$ also exhibited analgesic activity when administered to vivo and when administered intracerebroventricularly. In standard hot plate and tail flick assays, $DPE_2$ was more potent than the corresponding monomer, producing a dramatic stupor and persistent somnolence in test animals. Dimeric tetrapeptide enkephalin $DTE_{12}$ [$X=13(CH_2)_{12}-$]exhibited good analgesic activity but was less potent than $DPE_2$. In other bioassays, $DPE_2$ produced a rise in rat serum prolactin, after intracerebroventricular injection, which corresponds to that observed for other opiates and enkephalins. In an in vitro bioassay employing NG108-15 cells (a neuroblastoma-glioma hybrid cell line) stimulated by prostaglandin $E_1$ ($PGE_1$), $DPE_2$ showed an $IC_{50}$ of about 0.15 nM, consistent with the receptor affinity in binding assays.

For use as analgesics, the enkephalin dimers of the invention can be administered by either oral or parenteral routes, optionally in the form of their pharmaceutically acceptable salts, to relieve pain in mammals. The dosages are formulated for the chosen route of administration, and vary, inter-alia, according to the potency of the drug, the sensitivity of the patient, and the incidence of pain. Typically, dosages of active ingredient from about 0.1 mg to about 3 mg per kilogram of body weight are sufficient to achieve analgesia in ordinary therapeutic applications. The compounds are generally administered in conjunction with a conventional pharmaceutically acceptable carrier, either solid or liquid, with or without customary adjuvants.

The following examples are illustrative of the present invention.

EXAMPLES

The abbreviations used are: $DPE_n$, dimeric pentapeptide enkephalins [$Xd=(CH_2)_n-$], where n denotes the length of the methylene chain; TLC, thin-layer chromatography; Boc, tert-butoxycarbonyl; DD, dimeric dipeptides; DMF, N,N-dimethylformamide; HOBt, 1-hydroxybenzotriazole; EDC- HCl, 1-ethyl-3-(3-dimethylaminopropyl)carbodiimide hydrochloride; DP, dimeric pentapeptides; TFA, trifluoroacetic acid; NAL, naloxone; DAMEA, [D-Ala$^2$,Met$^5$]enkephalin amide; DADLE, [D-Ala$^2$,D-Leu$^5$]enkephalin; DALEA, [D-Ala$^2$,Leu$^5$]enkephalin amide.

EXAMPLE I

Synthesis of Dimeric Pentapeptide Enkephalins [$X=-(CH_2)_n-$, n is 2, 4, 6, 8, 10, or 12].

MATERIALS AND METHODS

Analytical Determinations

Melting points were measured utilizing a 6427-H10 Thomas-Hoover melting point apparatus and were uncorrected. TLC was carried out utilizing Silica Gel G (250 μm, Analtech). Optical rotations were measured with a Perkin-Elmer Model 241 MC polarimeter. Mass spectra were obtained using Californium-252 plasma desorption mass spectrometry, Amino acid analyses were performed on a Beckman Model 121MB amino acid analyzer.

Step 1. (Boc-Phe-Leu-NH-)$_2$. ($-CH_2-$)$_n$ (n=2, 4, 6, 8, 10 and 12). The dimers of the Boc-Phe-Leu dipeptide are designated $DD_n$, where n denotes the length of the methylene chain. To a solution of Boc-Phe-Leu-OH (833 mg, 2.20 mmoles) and α, ω -diaminoalkanes, $H_2N-(CH_2)_n-NH_2$ (1.00 mmole) in DMF (20 ml) were added HOBt (404 mg, 2.64 mmole) and EDC.HCl (464 mg, 2.42 mmole) at −10°. The reaction mixture was stirred for 2 hr at 0°, followed by incubation for 2 days at room temperature. The solvent was evaporated in vacuo, and ice-water was added to precipitate a solid. The solid collected was washed successively with 4% NaHCO$_3$, 10% citric acid, water, and petroleum ether. It was taken dried, and recrystallized twice from DMF-EtOAc-ether.

Step 2. (Boc-Tyr-D-Ala-Gly-Phe-Leu-NH-)$_2$. ($-CH_2-$)$_n$ (n=2–12). The dimers of the Boc-protected derivatives of the pentapeptide analogues are designated $DP_n$, wherein n again indicates the length of the methylene chain. Compound $DD_n$ (0.5 mmole) was dissolved in TFA (5 ml) at 0°. After 30 min. at 0°, the solution was evaporated to leave an oil, which was solidified by the addition of anhydrous ether, yielding (TFA.H-Phe-Leu-NH-)$_2$. ($-CH_2-$)$_n$. This TFA salt (0.5 mmole), Et$_3$N (0.14 ml, 1.0 mmole) and Boc-Tyr-D-Ala-Gly-OH (409 mg, 1.0 mmole) were dissolved in DMF (15 ml). To the solution were added HOBt (184 mg, 1.2 mmoles) and EDC . HCl (211 mg, 1.1. mmoles) at −10°, and the reaction mixture was treated as described for the $DD_n$ series in Step 1. Purifications were carried out by gel filtration on a Sephadex LH-20 column (2.2×96 cm) eluted with DMF, and then by recrystallization from DMF-EtOAc-ether.

Step 3. AcOH.H-Tyr-D-Ala-Gly-Phe-Leu-NH-)$_2$. ($-CH_2-$)$_n$ (n=2–12). The liberated dimetric pentapeptide analogues are designated as $DPE_n$, where n again indicates the methylene chain length. The compound $DP_n$ (0.25 mmole) was treated with TFA (5 ml) at 0° for 30 min. After evaporation of TFA the residual oil was dissolved in 30% AcOH and subjected to gel filtration on a column (2.2×145 cm) of Sephadex G-25 in 30% AcOH. The fractions containing a pure product by TLC were pooled and lyophilized repeatedly with aqueous AcOH. Homogeneity of the peptides was verified by ascending TLC in three different solvent systems (Table 1). For amino acid analysis, peptides were hydrolyzed in 6 M HCl for 24 hr at 110° in de-aerated tubes (data not given).

TABLE 1

Physical properties of
(AcOH.H—Tyr—D-Ala—Gly—Phe—Leu—NH—)$_2$:
(—CH$_2$—)$_m$ (DPE$_n$)

| DPE$_n$ | Yield % | Melting Point | $[\alpha]_D^{20}$ (C0.5, 95% AcOH) | TLC[a] R$_F$ |
|---|---|---|---|---|
| DPE$_2$ | 98 | 126° | +22.6° | 0.28 |
| DPE$_4$ | 98 | 149° | +21.0° | 0.29 |
| DPE$_6$ | 96 | 118° | +22.6° | 0.32 |
| DPE$_8$ | 87 | 111° | +23.4° | 0.35 |
| DPE$_{10}$ | 96 | 109° | +22.8° | 0.36 |
| DPE$_{12}$ | 98 | 108° | +22.2° | 0.38 |

[a]Solvent: n-BuOH—AcOH—H$_2$O (4:1:5, v/v, organic phase.)

The synthesis of dimeric analogues by the conventional solution methods as described here offers several advantages. (a) Cross linkages are built up by amide bond formation which makes the splitting of dimers by metabolic processes unlikely. (b) Synthesis of dimeric analogues can be carried out exactly like that of a monomeric analogue except that 2 equivalents of peptide acids are used. This means that a dimeric analogue can be obtained with essentially the same effort as monomeric pentapeptide enkephalins. No differences of reactivity were observed among the series of dimers. (c) Coupling reactions can be conducted by the water-soluble EDC-HOBt method and using the fragment intermediate Boc-Tyr-D-Ala-Gly-OH, which avoids the problem of racemization at the COOH terminus. This resulted in high yields of well characterized final products.

EXAMPLE II

Radioligand Binding Assay

Three binding assays using tracers of different selectivity were used to assess the activity of DPEn:[$^3$H] naloxone ($^3$H-NAL), which labels $\mu$ receptors; [$^{125}$I]-[D-Ala$^2$, D-Leu$^5$]-enkephalin ($^{125}$I-DADLE), which labels $\delta$; and [$^3$H]-[D-Ala$^2$, Met$^5$]-enkephalin amide ($^3$H-DAMEA), which labels both $\mu$ and $\delta$. Binding was studied in rat brain membranes at 26° C. in the presence of bacitracin (100 mg/ml) in absence of sodium ion (Table 2).

TABLE 2

ED$_{50}$ Values for DPEn in Three Radioligand
Assays: '$\mu$', Using H—Naloxone, '$\delta$', Using $^{125}$I—DADLE;
or 'Mixed $\delta$ and $\mu$', Using $^3$H—DAMEA.

| Enkephalins | ED$_{50}$ (nM) | | |
|---|---|---|---|
| | $^3$H—NAL | $^3$H DAMEA | $^{125}$I—DADLE |
| (Monomer) | | | |
| DALEA | 1.74 | 1.99 | 2.17 |
| (Dimers) | | | |
| DPE$_2$ | 1.78 | 1.01 | 0.27 |
| DPE$_4$ | 2.28 | 1.40 | 0.33 |
| DPE$_6$ | 2.61 | 1.53 | 0.43 |
| DPE$_8$ | 3.37 | 2.06 | 0.83 |
| DPE$_{10}$ | 5.82 | 3.99 | 1.95 |
| DPE$_{12}$ | 8.51 | 6.50 | 9.12 |
| Relative % error | ±22% | 28% | ±37% |

The ED$_{50}$ values of dimeric enkephalin are clearly lower in the $^{125}$T-DADLE binding assay than in the $^3$H-NAL assay, suggesting that their affinity for $\delta$ receptor is very high. If the potency of DPEn is normalized to that of the parent monomer (standard DALEA = 1), then the activities of dimeric enkephalins in the three binding assays can be compared as a function of the chain length (FIG. 1).

The most potent analog, DPE2, is seven times more potent than the monomer standard in binding to $\delta$ receptors ($^{125}$I-DADLE), but equivalent to monomer when binding to $\mu$ sites ($^3$H-NAL). Elongation of the methylene chain reduces activity in all the assays. For 4<n<10, dimeric enkephalins are more active than DALEA in a $\delta$ assay but less potent than DALEA in the $\mu$ assay. A chain length of 12 produces a severe drop of potency in both cases. In the $^3$H-DAMEA radioligand assay, the activity-length relationship is intermediate.

Figure 2:
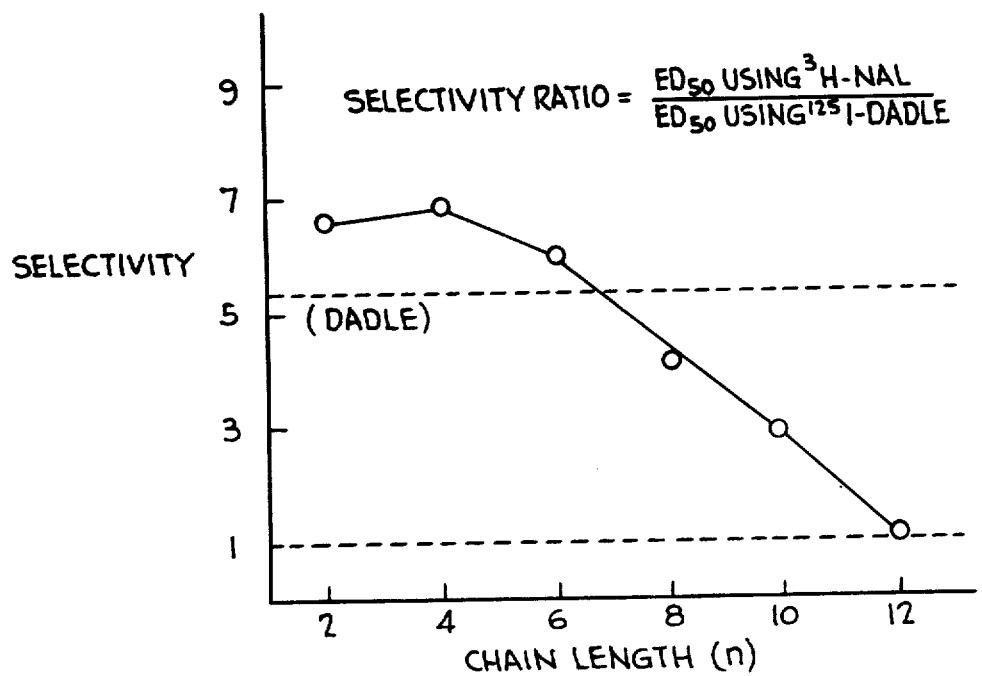
FIG. 2 is a graph of a selectivity ratio, defined as $ED_{50}$ for any given compound in the $^3H$-NAL assay, relative to its $ED_{50}$ in the $^{125}I$-DADLE assay, as a function of chain length (n).

The ratio of the ED$_{50}$ values for any peptide when using $^3$H-NAL as a tracer relative to its ED$_{50}$ when using $^{125}$I-DADLE furnishes a measure of the selectivity of peptides for $\delta$ and $\mu$ receptors. A completely nonselective compound with the same potency in both the assays would have a ratio of 1. The shorter the chains, the higher the selectivity of dimeric enkephalins for $\delta$ receptors (FIG. 2) Compounds DPE2, DPE4, DPE6 show greater selectivity for $\delta$ than DADLE itself. DPE12 shows no selectivity for $\delta$ relative to $\mu$ receptors.

What is claimed is:

1. A symmetrical dimeric enkephalin polypeptide capable of binding to neural opiate receptors of the formula

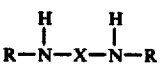

wherein:
X is a divalent 2,7-fluorene radical, C$_1$-C$_{22}$-alkylene, or a direct bond;
R is H-Tyr-D-Ala-Gly-Phe-Leu; H-Tyr-D-Ala-Bly-Phe; H-Tyr-D-Ala-Gly, or Phe-Leu; and
the R groups are the same.

2. The compound of claim 1, wherein X is a polymethylene chain of the formula —(CH$_2$)$_n$—, wherein n is from 1 to 22.

3. The compound of claim 2, wherein R is H-Tyr-D-Ala-Gly-Phe-Leu.

4. The compound of claim 2, wherein R is H-Tyr-D-Ala-Gly-Phe.

5. The compound of claim 1, wherein X is a direct bond.

6. The compound of claim 1, wherein X is a divalent 2,7-fluorene radical.

7. The compound of claim 2, wherein n is from 1 to 12 R is H-Tyr-D-Ala-Gly-Phe-Leu.

8. The compound of claim 2, wherin n is from 1 to 12 and R is Phe-Leu.

9. The compound of claim 5, wherein R is H-Tyr-D-Ala-Gly-Phe-Leu.

10. The compund of claim 6, wherein R is H-Tyr-D-Ala-Gly-Phe-Leu.

11. A therapeutic composition having analgesic activity comprising a compound of claim 1 and a pharmaceutically acceptable carrier.

12. A therapeutic composition having analgesic activity comprising an effective amount of compound of claim 3 and a pharmaceutically acceptable carrier.

13. A therapeutic composition having analgesic activity comprising an effective amount of compound of claim 4 and a pharmaceutically acceptable carrier.

14. A therapeutic composition having analgesic activity comprising an effective amount of compound of claim 6 and a pharmaceutically acceptable carrier.

15. A therapeutic composition having analgesic activity comprising an effective amount of compound of claim 7 and a pharmaceutically acceptable carrier.

16. A compound of the formula

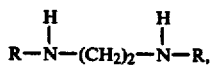

wherein R is H-Tyr-D-Ala-Gly-Phe-Leu.

17. A compound of the formula

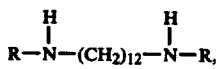

wherein R is H-Tyr-D-Ala-Gly-Phe.

18. A method of inducing analgesia in mammals, comprising administering a compound of the formula

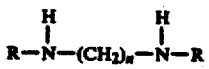

wherein R is H-Tyr-D-Ala-Gly-Phe-Leu, or H-Tyr-D-Ala-Gly-Phe; the R groups are the same; and n is from 1–22; to said mammal in an amount sufficient to alleviate pain.

19. The method of claim 18, wherein R is H-Tyr-D-Ala-Gly-Phe-Leu, and n is 2.

20. The method of claim 18, wherein R is H-Tyr-D-Ala-Gly-Phe and n is 12.